United States Patent [19]

Wilson et al.

[11] 4,156,662

[45] May 29, 1979

[54] 1-[3-(METHYLTHIO)BUTYRYL]-2,6,6-TRIMETHYL-CYCLOHEXENE AND THE 1,3-CYCLOHEXADIENE ANALOG IN PERFUMERY

[75] Inventors: Richard A. Wilson, Westfield; Braja D. Mookherjee, Holmdel; Anne S. Hruza, Brick Town; Manfred H. Vock, Locust; Louis S. Frederick, Holmdel; Joaquin F. Vinals, Red Bank, all of N.J.

[73] Assignee: International Flavors & Fragrances Inc., New York, N.Y.

[21] Appl. No.: 917,661

[22] Filed: Jun. 21, 1978

Related U.S. Application Data

[62] Division of Ser. No. 774,055, Mar. 3, 1977, Pat. No. 4,107,209.

[51] Int. Cl.² .............................................. C11B 9/00
[52] U.S. Cl. .............................. 252/522; 252/89 R; 252/174; 131/144; 424/69; 424/358; 426/533; 426/534
[58] Field of Search ......................................... 252/522

[56] References Cited

U.S. PATENT DOCUMENTS

| | | | |
|---|---|---|---|
| 3,900,520 | 8/1975 | Schenk et al. | 252/522 |
| 3,952,062 | 4/1976 | Lamparsky et al. | 252/522 |
| 4,020,171 | 4/1977 | Tsuchihashi | 252/522 |
| 4,031,034 | 6/1977 | Wilson et al. | 252/522 |
| 4,032,478 | 6/1977 | Lamparsky et al. | 252/522 |
| 4,065,408 | 12/1977 | Evers et al. | 252/522 |
| 4,081,480 | 3/1978 | Evers et al. | 252/522 |
| 4,094,824 | 6/1978 | Evers et al. | 252/522 |
| 4,107,209 | 8/1978 | Wilson et al. | 252/522 |

*Primary Examiner*—Veronica O'Keefe
*Attorney, Agent, or Firm*—Arthur L. Liberman; Franklin D. Wolffe

[57] ABSTRACT

The compounds 1-[3-(methylthio)butyryl]-2,6,6-trimethyl-cyclohexene and/or the corresponding 1,3-cyclohexadiene analog having the generic structure:

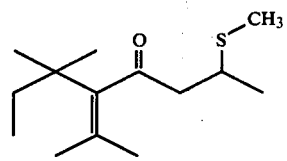

wherein the dashed line could be a single or a double carbon-carbon bond and processes and compositions containing same are described for the use in perfume augmenting and enhancing compositions and for use perfume aroma imparting compositions; produced by a process illustrated by the reaction:

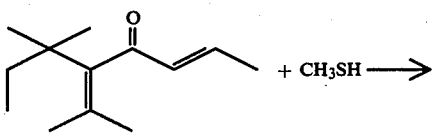

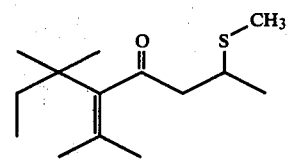

The above-mentioned compounds produce:
In perfumes, fruity, floral, natural rose oil-like and earthy aromas with potato top notes and minty, tomato vine, Brussel sprout-like and woody undertones.

5 Claims, 7 Drawing Figures

EXAMPLE I

PORTION OF GLC PROFILE

EXAMPLE I: PEAK A

EXAMPLE I: PEAK B

EXAMPLES I AND II

NMR SPECTRUM
SOLVENT: CDCl₃
SWEEP WIDTH: 2000 Hz.

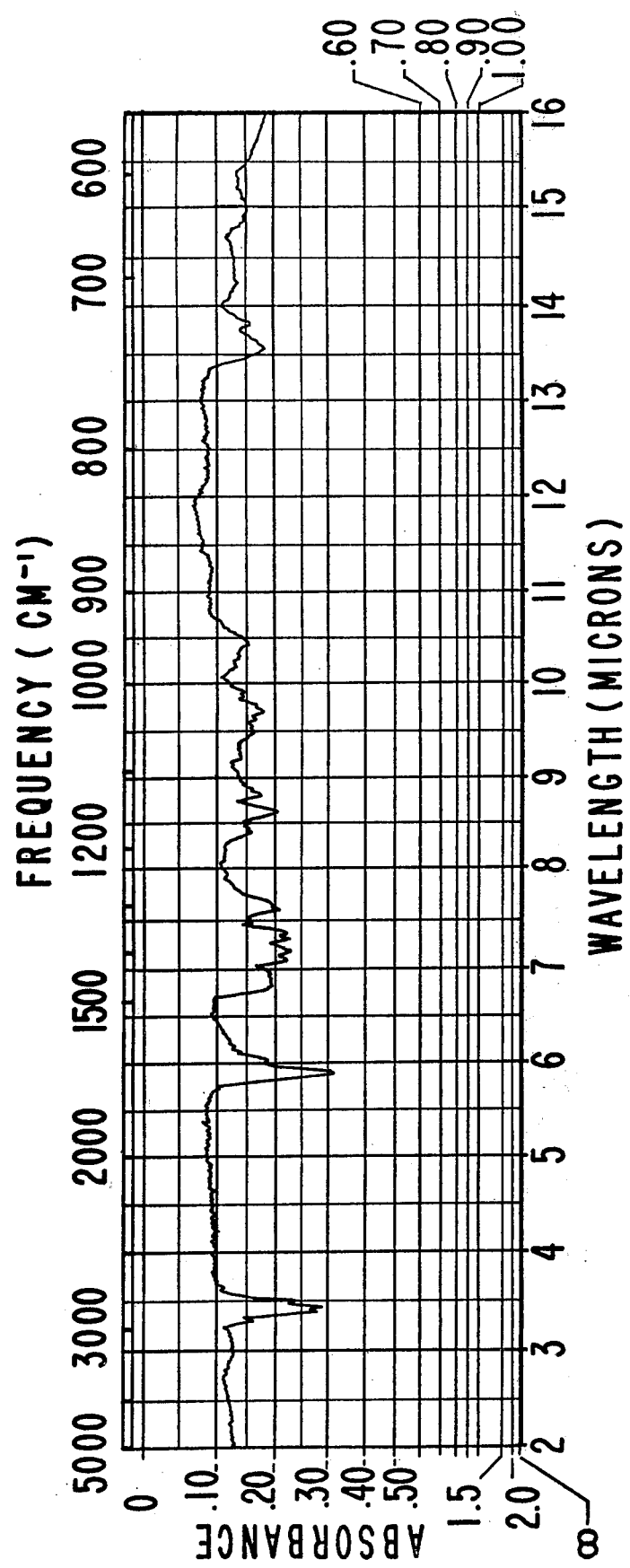

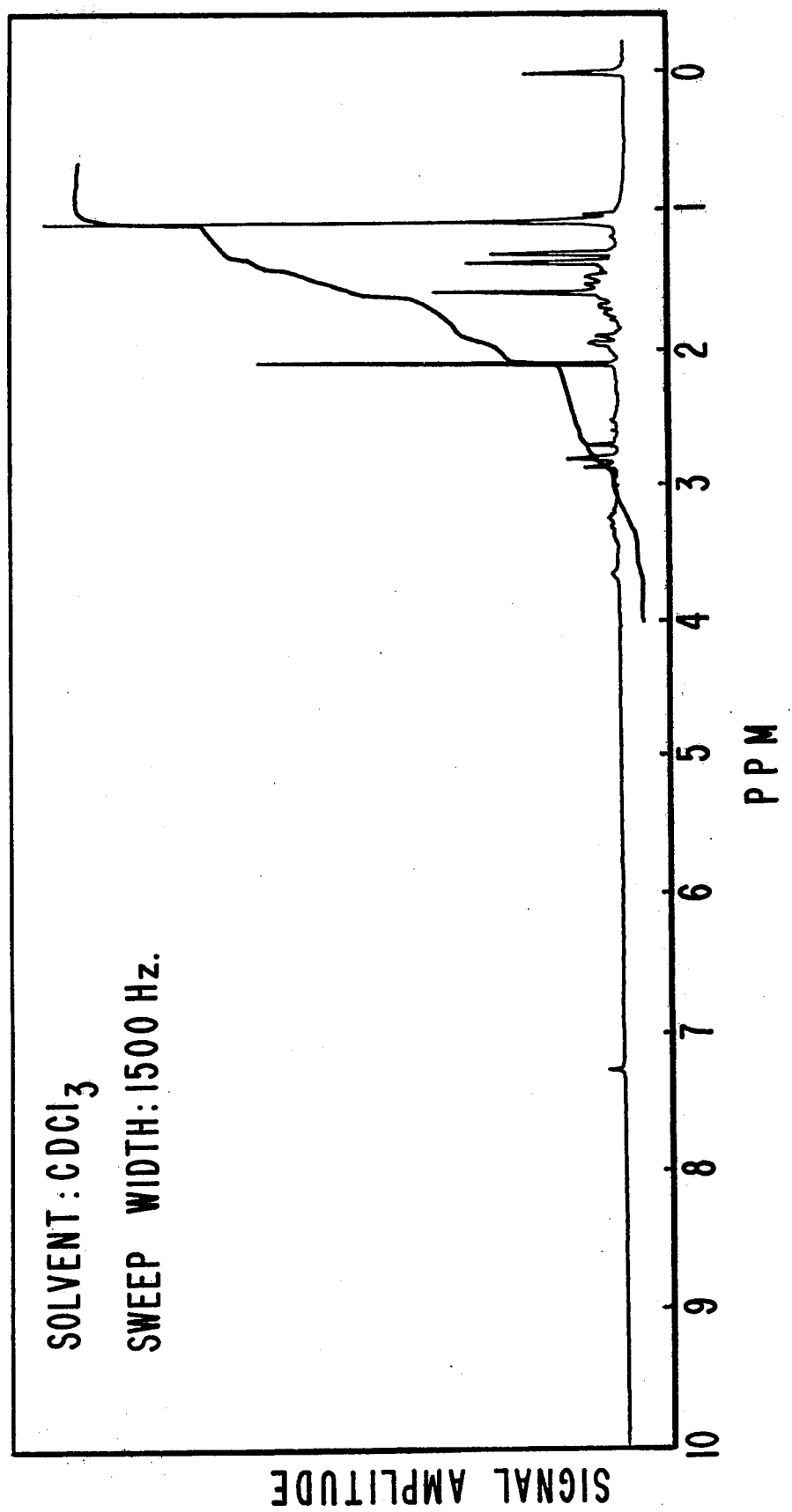

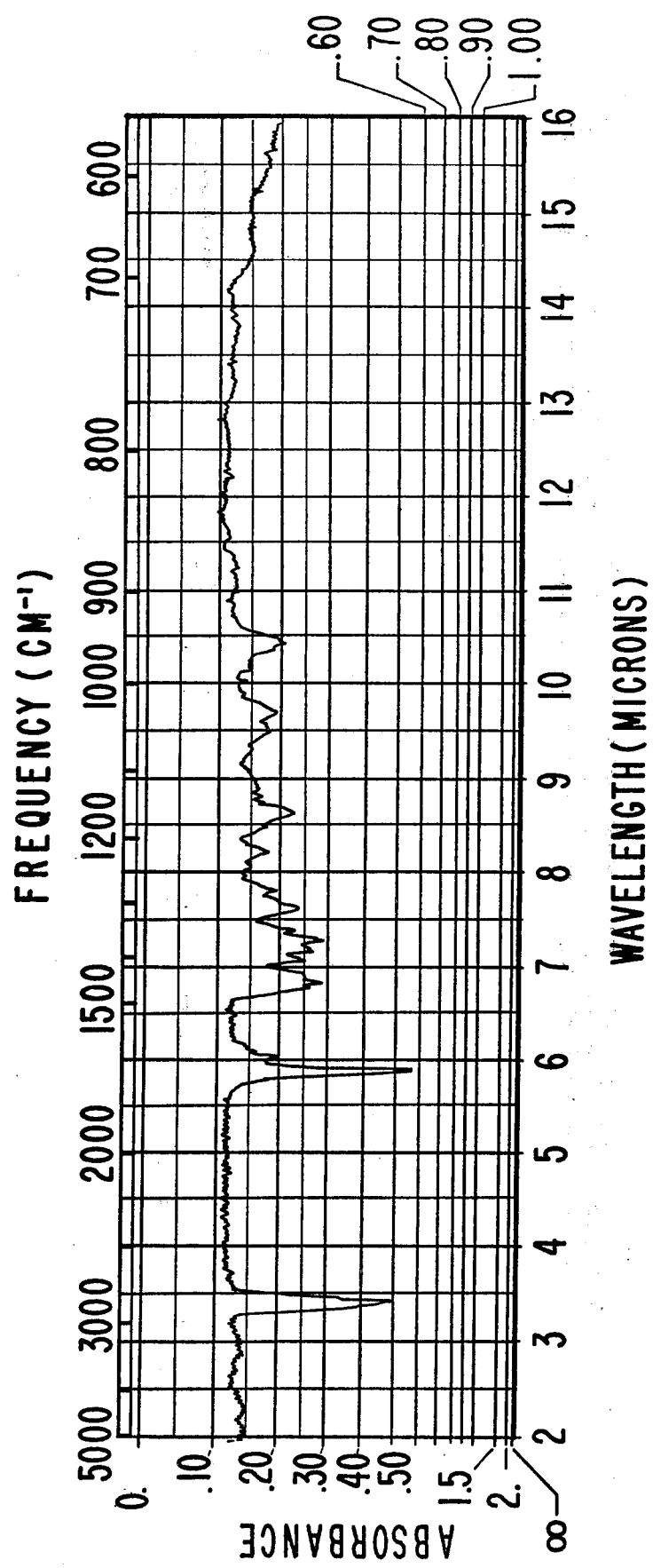

1-[3-(METHYLTHIO)BUTYRYL]-2,6,6-TRIMETHYL-CYCLOHEXENE AND THE 1,3-CYCLOHEXADIENE ANALOG IN PERFUMERY

This is a divisional of application Ser. No. 774,055, filed Mar. 3, 1977 now U.S. Pat. No. 4,107,209.

BACKGROUND OF THE INVENTION

The present invention relates to 1-[3-(methylthio)-butyryl]-2,6,6-trimethyl-cyclohexene and the corresponding 1,3-cyclohexadiene analog having the generic structure:

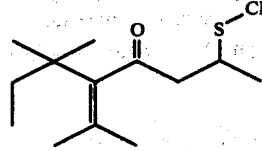

wherein the dashed line could be a single or a double carbon-carbon bond, produced by the process of reacting methyl mercaptan with "beta-damascenone" or "beta-damascone" according to the reaction:

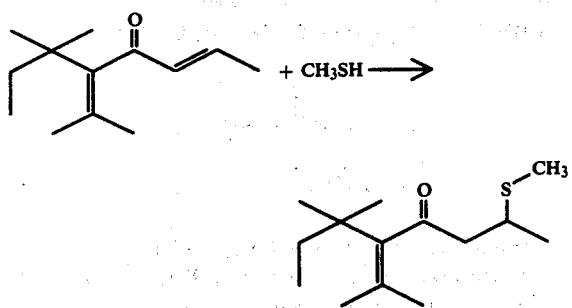

and novel compositions using such 1-[3-(methylthio)-butyryl]-2,6,6-trimethyl-cyclohexene and/or the corresponding 1,3-cyclohexadiene analog to augment or enhance the flavor and/or aroma of consumable materials.

There has been considerable work performed relating to substances which can be used to impart (augment or enhance) flavors and fragrances to (or in) various consumable materials. These substances are used to diminish the use of natural materials, some of which may be in short supply to provide more uniform properties in the finished product.

Sweet, black tea-like, tobacco-like, cocoa-like "damascenone-like," chocolate-like, dried fruit-like and rose petal-like aroma characteristics and sweet, black tea-like, cocoa-like, "damascenone-like," chocolate-like, tobacco-like, dried fruit-like and rose petal-like flavor characteristics are particularly desirable for many uses in the foodstuff, chewing gum, toothpaste and medicinal product flavor area. Sweet, honey-like, rich, slightly, fruity, dried fruit-like, hay tobacco-like, raspberry-like, blackcurrant-like, cedarwood-like, Virginia tobacco-like and woody notes are desirable in tobacco and tobacco flavor compositions especially where these notes appear both in the main stream and in the side stream on smoking as well as prior to smoking. Floral, natural rose oil-like and earthy aromas are especially desirable in several types of perfume compositions.

Sulfur containing cycloaliphatic ketones for use in augmenting or enhancing the organoleptic properties of foodstuffs and perfumes are well known in the prior art. U.S. Pat. No. 3,979,422 discloses compounds having the structures:

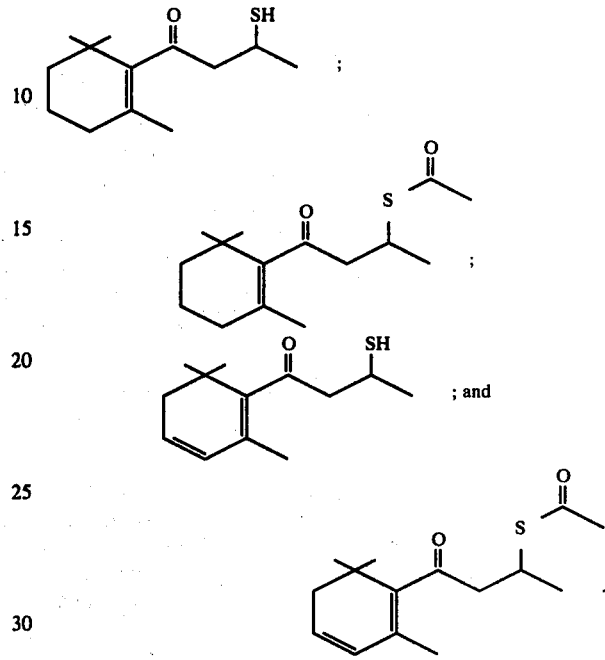

Alkylthio aliphatic ketones for use in augmenting or enhancing the organoleptic properties of foodstuffs are also well known in the prior art. U.S. Pat. No. 3,952,062 discloses such alkylthio aliphatic ketones, having the generic structure:

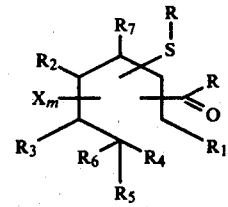

wherein $R^1$ represents hydrogen or together with $R^4$ represents a C—C bond, $R^2$ represents hydrogen or together with $R^6$ represents a dimethylmethylene group, or, when $R^6$ is isopropyl, together with $R^5$ represents a C—C bond, $R^3$ represents hydrogen or together with $R^6$ represents a dimethylmethylene group, $R^4$ represents hydrogen or together with $R^1$ represents a C—C bond, $R^5$ represents hydrogen or when $R^6$ signifies isopropyl together with $R^2$ represents a C—C bond, $R^6$ represents isopropyl or together with $R^2$ or with $R^3$ represents a dimethylmethylene group, $R^7$ represents methyl, X represents a C—C double bond taking the place of a C—C single bond, m =0 to 2, provided that when $R^2$, $R^3$ and $R^5$ represent hydrogen, $R^6$ represents isopropyl, $R^4$ together with $R^1$ represents a C—C bond, m =0.

The methylthio derivatives of the present invention are not, however, disclosed or referred to implicitly or explicitly in U.S. Pat. No. 3,952,062.

It is noteworthy that at column 3, of U.S. Pat. No. 3,952,062, the compounds having the structure:

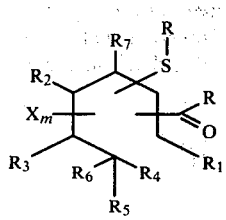

are indicated to be useful in foodstuff flavors and aroma where cabbage-like or onion-like aromas are desired. No such aromas are imparted or augmented or enhanced by the compounds of our invention.

Although the compounds of our invention having the generic structure:

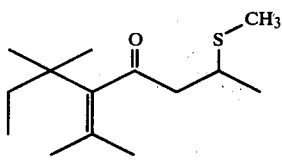

wherein the dashed line represents a carbon-carbon single bond or a carbon-carbon double bond have been determined to be existing in black tobacco oil, the compounds of our invention do not have organoleptic qualities which are even remotely similar to the organoleptic qualities of black tobacco oil.

Accordingly, the 1-[3-(methylthio)butyryl]-2,6,6-trimethyl-cyclohexene and/or the corresponding analog of our invention having the generic structure:

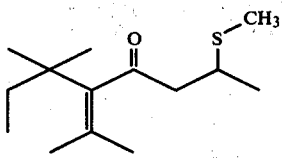

wherein the dashed line represents a carbon-carbon double bond or a carbon-carbon single bond, have properties which are unexpected, unobvious and advantageous when compared to black tobacco oil where these compounds are found, and when compared to the compounds of the prior art, specifically those of U.S. Pat. No. 3,952,062 and U.S. Pat. No. 3,979,422.

THE INVENTION

It has now been discovered that novel solid and liquid foodstuff, chewing gum, toothpaste and medicinal products and flavoring compositions having sweet, black tea-like, tobacco-like, damascenone-like, chocolate-like, dried fruit-like and rose petal-like and cocoa-like aroma characteristics as well as sweet, black tea-like, chocolate-like, damascenone-like, tobacco-like, dried fruit-like, rose petal-like and cocoa like flavor characteristics; novel perfume compositions having floral, natural rose oil-like and earthy aromas with potato top notes and minty, tomato vine, Brussel sprout-like and woody undertones; as well as novel tobacco and tobacco flavoring compositions having sweet, honey-like, rich, slightly fruity, dried fruit-like, hay tobacco-like, cedarwood-like, raspberry-like, blackcurrant-like, Virginia tobacco-like and woody notes both prior to and on smoking may be provided by the utilization of 1-[3-(methylthio)butyryl]-2,6,6-trimethyl-cyclohexene and/or the corresponding 1,3-cyclohexadiene analog having the generic structure:

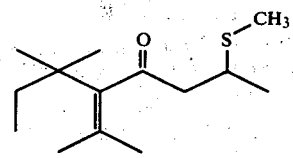

wherein the dashed line represents a carbon-carbon single bond or a carbon-carbon double bond in foodstuffs, chewing gum, toothpastes, medicinal products, perfume compositions, perfumed articles, colognes and tobaccos as well as tobacco substitutes. "β-damascenone" is a compound having the structure:

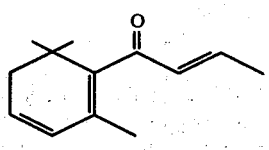

Its organoleptic properties and preparation are set forth in Swiss Pat. No. 520,479, issued on May 12, 1972.

"β-damascone" is a compound having the structure:

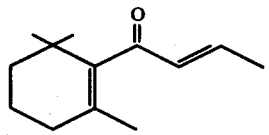

Its organoleptic properties and preparation are set forth in U.S. Pat. No. 3,927,107, issued on Dec. 16, 1975.

The 1-[3-(methylthio)butyryl]-2,6,6-trimethyl-cyclohexene and/or the corresponding 1,3-cyclohexadiene analog useful as indicated, supra, may be produced preferably by a process which involves reacting methyl mercaptan (CH$_3$SH) with "β-damascone" or "β-damascenone" according to the reaction:

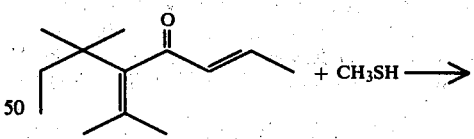

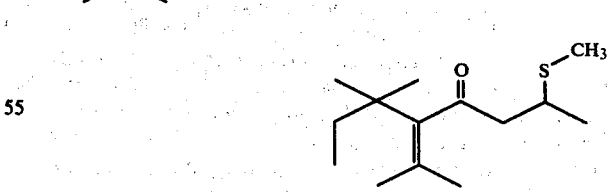

More specifically, the reactions carried out are as follows:

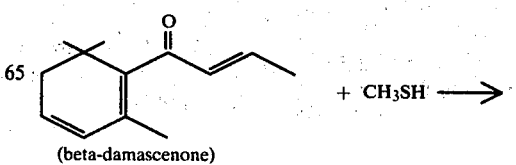

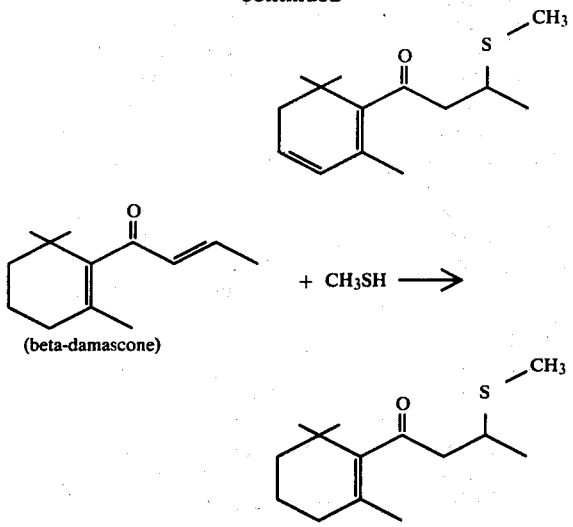

(beta-damascone) + CH₃SH ⟶

Our invention encompases the organoleptic uses of two compounds in particular having the structures and names as follows:

| STRUCTURE | NAME |
|---|---|
| 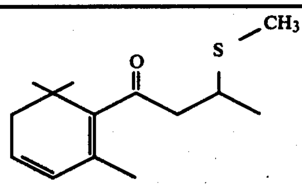 | 3-(methylthio)-1-(2,6,6-trimethyl-1,3-cyclohexadien-1-yl)-1-butanone<br>or<br>1-[3-methylthio(butyryl]-2,6,7-trimethyl-1,3-cyclo-hexadiene |
| 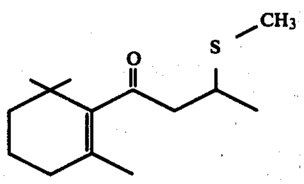 | 3-(methyl(thio)-1-(2,6,6-trimethyl-1-cyclohexen-1-yl)-1 butanone.<br>or<br>1-[3 (methylthio)butyryl]-2,6,6-trimethyl cyclohexene |

These compounds have the following organoelptic properties:

| STRUCTURE | FOOD FLAVOR PROPERTIES | TOBACCO FLAVOR PROPERTIES | PERFUMERY PROPERTIES |
|---|---|---|---|
| 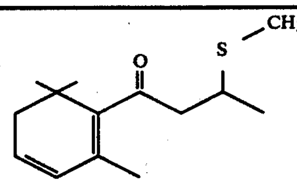 | Sweet, black-tea-like, tobacco-like, damascenone-like, chocolate-like, dried-fruit-like, rose-petal-like aroma characteristics with sweet, black-tea-like, chocolate-like, damascenone-like, tobacco-like, dried-fruit-like and rose-petal-like flavor characteristics. | Sweet-honey-like, rich, slightly-fruity, hay-tobacco-like, woody-like flavor characteristics prior to and on smoking in the main stream and in the side stream with sweet, floral and fruity nuances. | Floral and natural rose oil-like aroma nuances. |
| 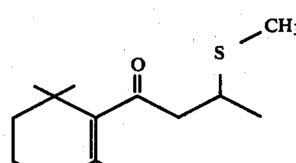 | Sweet, black-tea-like, cocoa-like and damascenone-like aroma characteristics with sweet, black-tea-like, cocoa-like and damascenone-like flavor characteristics. | Lingering rich, sweet, fruity, dried fruit-like, slightly floral, raspberry-like, blackcurrant-like aroma prior to and on smoking in both the main stream and side stream. | Earthy, potato-like top note, giving way to a minty, tomato vine/Brussel sprout nuance, with woody undertone. |

The 1-[3-(methylthio)butyryl]-2,6,6-trimethyl-cyclohexene and/or its corresponding 1,3-cyclohexadiene analog are capable of supplying and/or potentiating certain flavor and aroma notes usually lacking in many fruit flavors as well as tobacco flavors heretofore. Furthermore, the 1-3-(methylthio)butyryl]-2,6,6-trimethyl-cyclohexene and/or its corresponding 1,3-cyclohexadiene analog of our invention are capable of supplying certain fragrance notes usually lacking in many perfumery materials, for example, floral fragrances.

When 1-[(methylthio)butyryl]-2,6,6-trimethyl-cyclohexene and/or its corresponding 1,3-cyclohexadiene analog are used as fruit flavor adjuvants, the nature of the co-ingredients included with the said 1-[3-(methylthio)butyryl]-2,6,6-trimethyl-cyclohexene and/or its corresponding 1,3-cyclohexadiene analog in formulating the product composition will also serve to alter or enhance the organoleptic characteristics of the ultimate foodstuff treated therewith.

As used herein, the term "foodstuff" includes both solid and liquid ingestible materials which usually do, but need not, have nutritional value. Thus, foodstuffs includes soups, convenience foods, beverages, dairy products, candies, vegetables, cereals, soft drinks, snacks and the like.

As used herein, the term "medicinal products" includes both solids and liquids which are ingestible non-toxic materials which have medicinal value such as cough syrups, cough drops, aspirin and chewable medicinal tablets.

The term "chewing gum" is intended herein to be a foodstuff which is a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates one or more of the 1-[3methyl-thio)butyryl]-2,6,6-trimethyl-cyclohexene and/or its corresponding 1,3-cyclohexadiene analog of our invention, and, in addition, sweetening agents which may be sugars, including sucrose or dextrose and/or artificial sweeteners such as cyclamates or saccharin. Other optional ingredients may be present.

The term "augment" in its various forms is used herein to mean the supplying, modifying or imparting of a flavor or aroma characteristic, note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

Substances suitable for use herein as co-ingredients or flavoring adjuvants are well known in the art for such use, being extensively described in the relevant literature. It is required that any such material be "ingestibly acceptable", and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthically pleasing aroma and taste profile. Such material, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene(2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric nd curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, beta, beta-dimethylacrolein, n-hexanal, 2-hexenal, cis-3-hexenal, 2-heptenal, 4-(p-hydroxyphenyl)-2-butanone, alpha-ionone, beta-ionone, 2-methyl-3-butanone, 2-pentanone, 2-pentenal and propanal; alcohols such as 1-butanal, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, -pentenol, 1-penten-3-ol, p-hydroxyphenyl-2-ethanol, isoamyl alcohol, isofenchyl alcohol, phenyl-2-ethanol, alpha-terpineol, cis-terpineol hydrate; esters, such as butyl acetate, ethyl acetate, ethyl acetoacetate, ethyl benzoate, ethyl butyrate ethyl caproate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, methyl-2-methylbutyrate, propyl acetate, amyl acetate, amyl butyrate, benzyl salicylate, dimethyl anthranilate, ethyl methylphenylglycidate, ethyl succinate, isobutyl cinnamate and terpenyl acetate; essential oils, such as jasmine absolute, rose absolute, orris absolute, lemmon essential oil, Bulgarian rose, yara yara, ntural raspberry oil and vanilla; lactones; sulfides, e.g., methyl sulfide and other materials such as maltol, acetoin and acetals (e.g., 1,1-diethoxyethane, 1,1-dimethoxyethane and dimethoxymethane.

The specific flavoring adjuvant selected for use may be either solid or liuid depending upon the desired physical form of the ultimate product, i.e., foodstuff, whether simulated or natural, and should, in any event, be capable of providing an environment in which the 1-[3-(methylthio)butyryl]-2,6,6-trimethyl-cyclohexene and/or its corresponding 1,3-cyclohexadiene analog can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of 1-[3-methylthio)butyryl]-2,6,6-trimethyl-cyclohexene and/or its corresponding 1,3-cyclohexdiene analog employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected, (to be effective) be sufficient to augment or enhance the organoleptic characteristics of the parent composition, (whether foodstuff per se or flavoring composition).

The use of insufficient quantities of 1-[3-(methylthio)-butyryl]-2,6,6-trimethyl-cyclohexene and/or its corresponding 1,3-cyclohexadiene analog will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficientamount" is to be accorded a significance in the context of the present invention consistent with the obtention of desired flavoring effects.

Thus, and with respect to ultimate food compositions, it is found that quantities of 1-[3-(Methylthio)butyryl -2,6,6-trimethyl-cyclohexene and/or its corresponding 1,3-cyclohexadiene analog ranging from a small but effective amount, e.g., 0.5 parts per million up to about 20 parts per million by weight based on total composition are suitable. Concentrations in excess of the maximum quantity stated are not normally recommended, since they fail to prove commensurate enhancement of organoleptic properties. In those instances, wherein the 1-[3-(methylthio)butyryl]-2,6,6-trimethyl-cyclohexene and/or its corresponding 1,3-cyclohexadiene analog is added to the foodstuff as an integral component of a flavoring composition, it is, of course, essential that the total quantity of flavoring composition employed be sufficient to yield an effective 1-[3-(methylthio)-butyryl]-2,6,6-trimethyl-cyclohexene and/or its corresponding 1,3-cyclohexene analog concentration in the foodstuff product.

Food flavoring compositions prepared in accordance with the present invention preferably contain the 1-[3-(methylthio)butyryl]-2,6,6-trimethyl-cyclohexene and/or its corresponding 1,3-cyclohexadiene analog in concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 1-[3-(methylthio)butyryl]-2,6,6-trimethylcyclohexene and/or its corresponding 1,3-cyclohexadiene analog, with, for example, gum arabic, gum tragacanth, carrageenan and the like, and thereafter spray-drying the resultant mixture whereby to obtain the particular solid product. Pre-prepared flavor mixes in powder from, e.g., a fruit-flavored powered mix are obtained by mixing the dried solid components, e.g., starch, sugar and the like and 1-[3-(methylthio)-butyryl]-2,6,6-trimethylcyclohexene and/or its corresponding 1,3-cyclohexadiene analog in a dry blender until the requisite degree of uniformity is achieved.

It is presently preferred to combine with the 1-[3-methylthio)butyryl]-2,6,6-trimethyl-cyclohexene and/or its corresponding 1,3-cyclohexediene analog the following adjuvants:

p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;
Gamma-undecalactone;
Naphthyl ethyl ether;
Diacetyl;
Ethyl acetate;
Anethole;
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene); and
2-(4-hydroxy-4-methylpentyl) norbornadiene prepared according to U.S. application for Letters Patents Ser. No. 461,705, filed on Apr. 17, 1974.

An additional aspect of our invention provides an organoleptically improved smoking tobacco product and additives therefor, as well as methods of making the same which overcome specific problems heretofore encountered in which specific desired sweet honey-like, rich, slightly fruity, dried fruit-like, raspberry-like, blackcurrant-like, Virginia tobacco-like, damascenone-like, hay tobacco-like, woody and cedarwood flavor and aroma characteristics are created or enhanced and may be readily controlled and maintained at the desired uniform level regardless of variations in the tobacco components of the blend.

This invention further provides improved tobacco additives and methods whereby various desirable sweet honey-like, rich, slightly fruity, dried fruit-like, raspberry-like, blackcurrant-like, Virginia tobacco-like, damascenone-like, hay tobacco-like, woody and cedarwood flavor and aroma characteristics may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient 1-[3-(methylthio)butyryl]-2,6,6-trimethyl-cyclohexene and/or its corresponding 1,3-cyclohexadiene analog.

In addition to the 1-[3-(methylthio)butyryl]-2,6,6,-trimethyl-cyclohexene and/or its corresponding 1,3-cyclohexadiene analog of our invention, other flavoring and aroma additives may be added to the smoking tobacco material or substitute therefor either separately or in mixture with the 1-[3-(methylthio)butyryl]-2,6,6,-trimethyl-cyclohexene and/or its corresponding 1,3-cyclohexadiene analog as follows:

I. Synthetic Materials

Beta-ethyl-cinnamaldehyde;

Eugenol;
Dipentene;
β-Damascone;
β-Damascenone;
Maltol;
Ethyl maltol;
Delta undecalactone;
Delta decalactone;
Benzaldehyde
Amyl acetate;
Ethyl butyrate;
Ethyl valerate;
Ethyl acetate;
2-Hexenol-1,2-methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naphtho-(2,1-b)-furan;
4-Hydroxy hexanoic acid, gamma lactone;
Polyisoprenoid hydrocarbons defined in Example V of U.S. Pat. No. 3,589,372, issued on June 29, 1971.

II. Natural Oils

Celery seed oil;
Coffee extract;
Bergamot Oil;
Cocoa extract;
Nutmeg oil; and
Origanum oil.

An aroma and flavoring concentrate containing 1-[3-(methylthio)butyryl]-2,6,6-trimethyl-cyclohexene and/or its corresponding 1,3-cyclohexadiene analog and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as the augmentation, or the enhancement or the imparting of the sweet, honey-like, fruity, woody, cedarwood, dried fruit-like, raspberry-like, blackcurrant-like, Virginia tobacco-like notes are concerned, we have found that satisfactory results are obtained if the proportion by weight of the sum total 1-[3-(methylthio)butyryl]-2,6,6-trimethyl-cyclohexene and/or its corresponding 1,3-cyclohexadiene analog to smoking tobacco material is between 250 ppm and 1,500 ppm (0.025%–1.5%) of the active ingredients to the smoking tobacco material. We have further found that satisfactory results are obtained if the proportion by weight of the sum total of 1-[3-(methylthio)butyryl]-2,6,6-trimethyl-cyclohexene and/or its corresponding 1,3-cyclohexadiene analog used to flavoring material is between 2,500 and 10,000 ppm (0.25%–1.5%).

Any convenient method for incorporating the 1-[3-(methylthio)butyryl]-2,6,6-trimethyl-cyclohexene and/or its corresponding 1,3-cyclohexadiene analog in the botacco product may be employed. Thus, the 1-[3-(methylthio)butyryl]-2,6,6-trimethyl-cyclohexene and/or its corresponding 1,3-cyclohexadiene analog taken alone or along with other flavoring additives may be dissolved in a suitable solvent such as ethanol, n-pentane, diethyl ether and/or other volatile organic solvents and the resulting solution may either be sprayed on the cured, cased and blended tobacco material or the tobacco material may be dipped into such solution. Under certain circumstances, a solution of the 1-[3-(methylthio)butyryl]-2,6,6-trimethyl-cyclohexene and/or its corresponding 1,3-cyclohexadiene analog taken along or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the 1-[3-(methylthio)butyryl]-2,6,6-trimethyl-cyclohexene and/or its corresponding 1,3-cyclohexadiene analog in excess of the amounts or concentrations above indicated so that when blended with other tobaccos, the final product will have the percentage within the indicated range.

In accordance with one specific example of our invention, an aged, cured and shredded domestic burley tobacco is spread with a 20% ethyl alcohol solution of 1-[3-(methylthio)butyryl]-2,6,6-trimethyl-cyclohexene and/or its corresponding 1,3-cyclohexadiene in an amount to provide a tobacco composition containing 800 ppm by weight of 1-[3-(methylthio)butyryl]-2,6,6-trimethyl-cyclohexene and/or its corresponding 1,3-cyclohexadiene analog on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweet, rich, floral, fruity, hay tobacco-like, honey-like, cedarwood-like and Virginia tobacco-like.

While our invention is particularly useful in the manufacture of smoking tobacco, such as cigarette tobacco, cigar tobacco and pipe tobacco, other tobacco products formed from sheeted tobacco dust or fines may also be used. Likewise, the 1-[3-(methylthio)butyryl]-2,6,6-trimethyl-cyclohexene and/or its corresponding 1,3-cyclohexadiene analog of our invention can be incorporated with materials such as filter tip materials, seam paste, packaging materials and the like which are used along with tobacco to form a product adapted for smoking. Furthermore, the 1-[3-(methylthio)butyryl]-2,6,6-trimethyl-cyclohexene and/or its corresponding 1,3-cyclohexadiene analog can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The 1-[3-(methylthio)butyryl]-2,6,6-trimethyl-cyclohexene and/or its corresponding 1,3-cyclohexadiene analog and one or more auxiliary perfume ingredients, including, for example, alcohols, aldehydes, nitriles, esters, other ketones, cyclic esters, synthetic essential oils, and natural essential oils, may be admixed so that the combined odor of the individual components produce a pleasant and desired fragrance, particularly and preferably in floral fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute particular olfactory characteristics, but the over-all effect of the perfume composition will be the sum of the effects of each of the ingredients. Thus, the 1-[3-(methylthio)butyryl]-2,6,6-trimethyl-cyclohexene and/or its corresponding 1,3-cyclohexadiene analog can be used to alter the aroma characteristics of a perfume composition, for example by utilizing or moderating the olfactory reaction contributed by another ingredient in the composition.

The amount of 1-[3-(methylthio)butyryl]-2,6,6-trimethyl-cyclohexene and/or its corresponding 1,3-cyclohexadiene analog of our invention which will be effective in perfume compositions depends on many factors, including the other ingredients, their amounts and the effects which are desired. It has been found that perfume compositions containing as little as 0.1% of 1-[3-(methylthio)butyryl]-2,6,6-trimethyl-cyclohexene and/or its corresponding 1,3-cyclohexadiene analog (e.g., 0.05%) can be used to impart floral and natural rose oil-like odor to soaps, cosmetics or other products. The amount employed can range up to 10% of the fragrance components and will depend on considerations of cost, nature of the end product, the effect desired on the finished product and the particular fragrance sought.

The 1-[3-(methylthio)butyryl]-2,6,6-trimethyl-cyclohexene and/or its corresponding 1,3-cyclohexadiene analog is useful, taken alone or in perfume compositions as an olfactory component in detergents and soaps, space odorants and deodorants, perfumes, colognes, toilet water, bath preparations, such as bath oils, and bath solids; hair preparations, such as lacquers, brilliantines, pomades and shampoos; cosmetics preparations, such as creams, deodorants, hand lotions and sun screens; powders, such as talcs, dusting powders, face powders and the like, When used as an olfactory component, as little as 1% of the 1-[3-(methylthio)butyryl]-2,6,6-trimethyl-cyclohexene and/or its corresponding 1,3-cyclohexadiene analog will suffice to impart a natural rose oil-like or earthy and woody note(s) to floral formulations. Generally, no more than 3% of 1-[3-(methylthio)butyryl]-2,6,6-trimethyl-cyclohexene and/or its corresponding 1,3-cyclohexadiene analog based on the ultimate end product is required in the perfume composition.

In addition, the perfume composition or fragrance composition of our invention can contain a vehicle, or carrier for the 1-[3-(methylthio)butyryl]-2,6,6-trimethyl-cyclohexene and/or its corresponding 1,3-cyclohexadiene analog. The vehicle can be a liquid such as a non-toxic alcohol, a non-toxic glycol, or the like. The carrier can also be an absorbent solid, such as a gum (e.g., gum arabic) or components for encapsulating the composition (such as gelatin).

It will be apparent that 1-[3-(methylthio)butyryl]-2,6,6-trimethyl-cyclohexene and/or its corresponding 1,3-cyclohexadiene analog can be utilized to alter the sensory properties, particularly organoleptic properties, such as flavors and/or fragrances of a wide variety of consumable materials.

The following examples are illustrative and the invention is to be considered to be restricted thereto only as indicated in the appended claims. These examples serve to illustrate processes for producing the 1-[3-(methylthio)butyryl]-2,6,6-trimethyl-cyclohexene and/or its corresponding 1,3-cyclohexadiene analog useful in our invention and processes for using the 1-[3-(methylthio)butyryl]-2,6,6-trimethyl-cyclohexene and/or its corresponding 1,3-cyclohexadiene analog of our invention for their organoleptic properties.

All parts and percentages given herein are by weight unless otherwise specified.

EXAMPLE I

Extraction of 1-[3-(Methylthio)Butyryl]-2,6,6-Trimethyl-Cyclohexane and its Corresponding 1,3-Cyclohexadiene Analog from Black Tobacco 560 lbs of black tobacco lamina obtained from the Dominican Republic is ground and subjected to steam distillation under atmospheric pressure. The distillate is extracted with methylene chloride. The extract is then dried, partially concentrated, and separated into acidic (phenolic), basic and neutral fractions by back extraction with O.IN NaOH and O.IN HCl respectively. When these fractions are concentrated, the acidic (phenolic) fraction totals 12 grams, the basic fraction totals 250 grams and the neutral fraction totals 100 grams. The neutral oil is treated with Girard-T reagent to concentrate carbonyls. This fraction totals 4 grams of oil. The "carbonyl-poor" fraction, which totals 89 grams, is subjected to adsorption chromatography on activity grade II silic gel in isopentane and fractions are eluted with increasing proportions of ether: isopentane. Fraction # 14 which is eluted with 4% ether in isopentane totals 0.74 grams of oil and is subjected to GLC/MS analysis on a 400'×0.032" glass capillary column coated with SE-30 liquid phase. FIG. 1 sets forth a portion of the GLC profile in the vicinity of two peaks, "B" and "A" subsequently identified as consisting of the 1-[3-(methylthio)butyryll]-2,6,6-trimethyl-cyclohexene and its 1,3-cyclohexadiene analog, respectively, of our invention. The scan of FIG. 2 is obtained on peak "A" and the scan of FIG. 3 on peak "B." The GLC retention times of these two peaks are determined relative to a series of ethyl esters of the normal alkanoic acids, $C_1$–$C_{10}$, $C_{12}$, $C_{14}$ and $C_{16}$. Peak "A" has a relative retention time ($I_E$) of 13.00 and the $I_E$ of peak "B" is calculated to be 13.25. The parent ion of peak "A" is 238 and that of peak "B", is 240. In each case the M+2 ion suggests the presence of one S atom in each molecule and the M−47 fragmentation of each is consistent with the loss of a $CH_3$-S group. The major fragments of 121 and 149 for peak "A" and 123/151 for peak "B" are suggestive of fragmentation α to the carbonyl group in the β-damascenone/β-damascone series.

The methylthio additives of β-damascenone and β-damascone are synthezied according to the procedures given in Examples II and III respectively. The mass spectra and GLC retention times of the synthetic products are superimposable on those of peaks "A" and "B" respectively and the NMRs for each of the synthetic materials indicate the absence of allylic protons, therefore peaks "A" and "B" are assigned the structures:

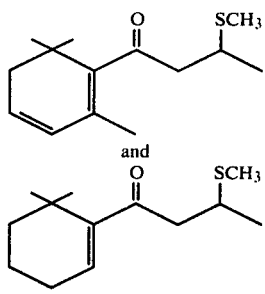

The NMR (nuclear magnetic resonance) spectrum for peak "A" which consists of the compound 1-[3-(methylthio)butyryl]-2,6,6-trimethyl-1,3-cyclohexadiene having the structure:

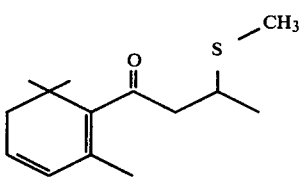

is set forth in FIG. 4. The NMR analysis is as follows:

| | | |
|---|---|---|
| 1.09 ppm (s) | gem dimethyl protons | 6 H |
| 1.34 (d) | CH$_3$—C—S— | 3 H |
| 1.74 (s) | =C—CH$_3$ | 3 H |
| 2.14 (s) | CH$_3$—S— | } 5 H |
| 2.12 (m) | —CH$_2$— | |
| 2.82 (m) | $\begin{array}{c}\text{S}\quad\text{O}\\ \mid\quad\parallel\\ -\text{C}-\text{CH}_2-\text{C}-\\ \mid\end{array}$ | 2 H |
| 3.28 (m) | $\begin{array}{c}\mid\\ \text{H}-\text{C}-\text{S}-\\ \mid\end{array}$ | 1 H |
| 5.81 (broad s) | olefinic protons | 2 H |

The infra-red spectrum for 1-[3-(methylthio)butyryl]-2,6,6-trimethyl-1,3-cyclohexadiene is set forth in FIG. 5.

The mass spectral analysis for 1-[3-(methylthio)butyryl]-2,6,6-trimethyl-1,3-cyclohexadiene is as follows:

| m/e | relative intensity |
|---|---|
| 39 | 27 |
| 41 | 86 |
| 43 | 38 |
| 55 | 21 |
| 69 | 58 |
| 75 | 100 |
| 80 | 34 |
| 91 | 29 |
| 105 | 48 |
| 117 | 29 |
| 121 | 61 |
| 133 | 19 |
| 149 | 43 |
| 175 | 3 |
| 190 | 2 |
| 223 | 12 |
| 238p | 5 |

The NMR spectrum for 1-[3-(methylthio)butyryl]-2,6,6-trimethyl-cyclohexene is set forth in FIG. 6.

The NMR analysis is as follows:

| | | |
|---|---|---|
| 1.70 ppm (s) | gem dimethyl protons | 6 H |
| 1.34 (d) | CH$_3$—C—S— | } |
| 1.59 (s) | =C—CH$_3$ | } 10 H |
| 1.78–1.42 (m) | —CH$_2$— | |
| 1.93 (m) | =C—CH$_2$— | 2 H |
| 2.12 (s) | CH$_3$—S— | 3 H |
| 2.80 (m) | $\begin{array}{c}\mid\\ -\text{CH}_2-\text{C}=\text{O}\\ \mid\end{array}$ | 2 H |
| 3.26 | $\begin{array}{c}\mid\\ \text{HC}-\text{S}-\\ \mid\end{array}$ | 1 H |

The infra-red spectrum for 1-[3-(methylthio)butyryl]-2,6,6-trimethyl-cyclohexene is set forth in FIG. 7.

The mass spectral analysis for 1-[3-(methylthio)butyryl]-2,6,6-trimethyl-cyclohexene is as follows:

| m/e | relative intensity |
|---|---|
| 41 | 17 |
| 43 | 11 |
| 69 | 18 |
| 75 | 33 |
| 81 | 26 |
| 89 | 47 |
| 123 | 47 |
| 151 | 100 |
| 177 | 6 |
| 193 | 7 |
| 225 | 5 |
| 240p | 32 |

EXAMPLE II

Preparation of 3-(Methylthio)1-(2,6,6-trimethyl-1,3-cyclohexadien-1-yl-1-Butanone Reaction:

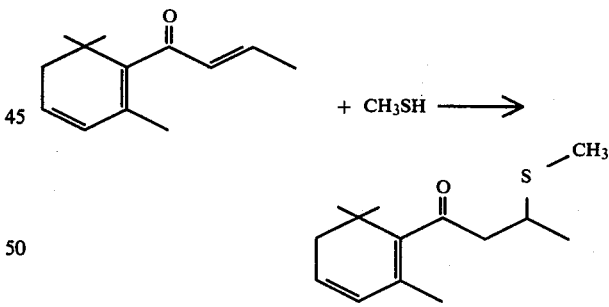

In a 50-ml, three-necked, round-bottom flask equipped with a magnetic stirring assembly, a tube submerged for the introduction of gas, an immersion thermometer and a dry ice isopropanol condenser, the outlet of which leads through a 50% alkali trap to the hood sink, is placed 8.3 grams of beta-damascenone and approximately 1 gram of triethylamine. Gaseous methyl mercaptan is introduced into the stirred reaction mixture which is maintained at 10° C. Addition is continued for approximately one hour and then stopped. The stirred reaction mix is allowed to attain room temperature, and the reaction mix is stirred overnight at room temperature. The next morning the light yellow reaction mix is transferred to 50 ml of ether in a separatory funnel and washed twice with dilute sulfuric acid, twice with saturated sodium bicarbonate solution, and then with saturated saline solution until the wash is neutral. The dried ether layer is stripped of solvent on a 'rotovap' and GLC of the residue on an ⅛'×10" stainless steel, 5% carbowax 20 M column isothermally at 190° C. shows one major late eluting peak which is trapped for infra-red and nuclear magnetic resonance/mass spectral analyses. Infra-red analysis suggests that the cyclohexadienyl ring structure is intact and in conjugation with the side chain ketone which is, however, now out of cross conjugation. Therefore, reaction appears to have occurred at the side chain olefinic site. Mass spectral analysis shows a molecular weight of 238, and the proper fragmentation for the proposed structure. The mass spectral analysis also is a satisfactory match with the scan for peak "A" as set forth in Example I. This peak has an $I_E$ on SE-30 of 13.00. A trap of the synthetic material is run for $I_E$ and the $I_E$ on SE-30 is 13.08.

They are thus considered to be the same compound, nuclear magnetic resonance showing the absence of allylic protons. The structure is then deduced to be:

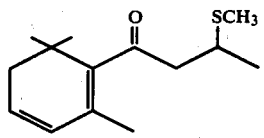

The product is subjected to vacuum fractional distillation at 2.95 mm Hg. Six fractions plus residue are obtained, the highest purity of which is 87.8%. All fractions still smell strongly of CH₃SH as if a small amount has formed during the distillation. To permit the evaluation of pure material, it is subjected to preparative gas liquid chromatography on a 10'×¼" carbowax 20M column.

The NMR spectrum is set forth in FIG. 4.
The IR spectrum is set forth in FIG. 5.
The mass spectral analysis is as follows:

| m/e | relative intensity |
|---|---|
| 39 | 27 |
| 41 | 86 |
| 43 | 38 |
| 55 | 21 |
| 69 | 58 |
| 75 | 100 |
| 80 | 34 |
| 91 | 29 |
| 105 | 48 |
| 117 | 29 |
| 121 | 61 |
| 133 | 19 |
| 149 | 43 |
| 175 | 3 |
| 190 | 2 |
| 223 | 12 |
| 238p | 5 |

EXAMPLE III

Preparation of 1-[3-(Methylthio)Butyryl]-2,2,6-Trimethyl-Cyclohexene-1

Reaction:

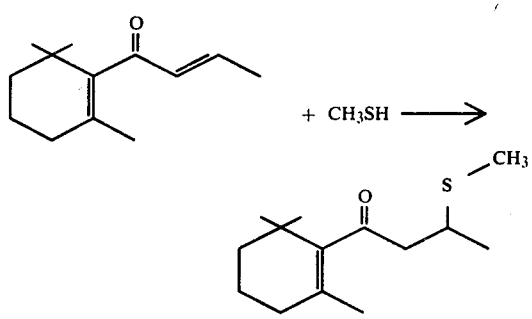

In the same reaction apparatus used for Example II is placed β-damascone weighing approximately 6 grams. Approximately 1 gram of triethyl amine is added, and the stirred mix is treated with gaseous CH₃SH for approximately 2 hours at room temperature. Addition of CH₃SH is stopped and the reaction mix is stirred overnight and then worked up in the same manner as the product of Example II. GLC of the residue on carbowax 20M shows that all of the β-damascone has reacted. A trap of the major peak is submitted for mass spectral analysis, and the proper molecular weight (240) and fragmentation for the following structure is observed:

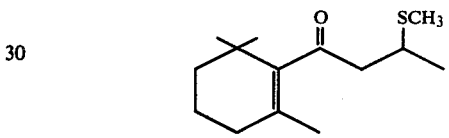

The scan for peak B of FIG. 3 matches the mass spectrum of the synthetic material. The $I_E$ of the synthetic material on SE-30 is 13.20, and that of the peak corresponding to the above scan is 13.29.

The NMR spectrum is set forth in FIG. 6.
The Infra-red spectrum is set forth in FIG. 7.
The mass spectral analysis is as follows:

| m/e | relative intensity |
|---|---|
| 41 | 17 |
| 43 | 11 |
| 69 | 18 |
| 75 | 33 |
| 81 | 26 |
| 89 | 47 |
| 123 | 47 |
| 151 | 100 |
| 177 | 6 |
| 193 | 7 |
| 225 | 5 |
| 240p | 32 |

EXAMPLE IV

Basic Raspberry Formulation Containing 3-(Methylthio)-1-(2,6,6-Trimethyl-1,3-Cyclohexadien-1-yl)1-Butanone The following basic raspberry formulation is prepared:

| Ingredients | Parts by Weight |
|---|---|
| Vanillin | 2 |
| Maltol | 4 |
| Para-Hydroxybenzylacetone | 5 |
| α-Ionone (10% in propylene | |

| Ingredients | Parts by Weight |
| --- | --- |
| glycol) | 2 |
| Ethyl butyrate | 6 |
| Ethyl acetate | 16 |
| Dimethylsulfide | 1 |
| Isobutylacetate | 14 |
| Acetic acid | 10 |
| Acetaldehyde | 10 |
| Propylene glycol | 930 |

The basic raspberry formulation is divided into two parts. To the first part 0.1% by weight of 3-(methylthio)-1-(2,6,6-trimethyl-1,3-cyclohexadien-1yl)-1-butanone prepared according to Example II is added. Both flavors with and without the additional material are compared at the rate of 100 parts per million in water by a bench-panel consisting of four people. The raspberry flavor with the addition of 3-(methylthio)-1-(2,6,6-trimethyl-1,3-cyclohexadien-1-yl)-1-butanone is considered not only stronger but as having a more raspberry juice-like character and having more of the desired raspberry seed or kernel note. The taste is closer to the ripe raspberry with pleasant tea and raspberry kernel notes. Therefore all panel members prefer the flavor with the addition of this flavor chemical.

EXAMPLE V

Basic Raspberry Flavor Formulation Containing 3-(Methylthio)-1-(2,6,6-Trimethyl-1-Cyclohexen-1-yl)-1-Butanone The following basic raspberry formulation is prepared:

| Ingredients | Parts by Weight |
| --- | --- |
| Vanillin | 2 |
| Maltol | 4 |
| Para-Hydroxybenzylacetone | 5 |
| α-Ionone (10% in propylene glycol) | 2 |
| Ethyl butyrate | 6 |
| Ethyl acetate | 16 |
| Dimethylsulfide | 1 |
| Isobutylacetate | 14 |
| Acetic acid | 10 |
| Acetaldehyde | 10 |
| Propylene glycol | 930 |

The formulation is divided into two parts. To one of the parts 0.1% by weight of 3-(methylthio)-1-(2,6,6-trimethyl-1-cyclohexen-1-yl)-1-butanone prepared according to Example III is added. To the second part of the basic raspberry formulation nothing else is added. Both formulations with and without the additional material are compared at the rate of 100 ppm (parts per million) in water by a bench panel. All members of the bench panel prefer the raspberry flavor with the addition of (3-methylthio)-1-(2,6,6-trimethyl-1-cyclohexen-1-yl)-1-butanone. The aroma is sweeter and more raspberry syrup-like, and the taste has a more raspberry distillate, black tea-like character and a raspberry kernel note.

EXAMPLE VI

Perfume Formulation Containing 2,2,6-Trimethyl-1-[3-(Methylthio) Butyryl]-1,3-Cyclohexadiene The following floral perfume formulation is prepared:

| Ingredients | Parts by Weight |
| --- | --- |
| Phenylethyl alcohol | 25 |
| Rhodinol | 22 |
| Hydroxycitronellal | 6 |
| Linalool | 5 |
| Cinnamic alcohol | 3 |
| Alpha ionone | 15 |
| Amyl acetate (1% in diethylphthalate) | 6 |
| Vetiverol | 2 |
| Ylang-ylang oil | 3 |
| Nerol | 2 |
| Musk ketone | 3 |
| Vanillin (10% in diethylphthalate) | 2 |
| Styrax essence | 1 |
| 2,2,6-trimethyl-1-[3-(methylthio)butyryl]-1,3-cyclohexadiene (produced according to Example II) | 5 |

The product of Example II itself has a sweet, rosey, floral, cured tobacco note. It gives lift and a more natural floralcy to the fragrance in which it is incorporated. Although it was incorporated above at a level of 5% by weight, it may be effectively used at from 0.1 up to 10% by weight in such floral formulations. For special effects it may be used as high as 50% by weight. Addition of the product of Example II to the instant fragrance, greatly increases its esthetic qualities and gives the olfactory illusion of the presence of natural rose oil.

EXAMPLE VII

Tobacco Formulation

A tobacco mixture is produced by admixing the following ingredients:

| Ingredients | Parts by weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1000 ppm of 3-(methylthio)-1-(2,6,6-trimethyl-1,3-cyclohexadien-1-yl)-1-butanone produced according to the process of Example II. The control cigarettes not containing the 3-(methylthio)-1-(2,6,6-trimethyl-1,3-cyclohexadien-1-yl)-1-butanone produced according to the process of Example II and the experimental cigarettes which contain the 3-(methylthio)-1-(2,6,6-trimethyl-1,3-cyclohexadien- 1yl1-butanone produced according to the process of Example II are evaluated by paired comparison and the results are as follows:

The experimental cigarettes are found to have more body and to be, on smoking, more tobacco-like, more aromatic, sweet, fruity, hay-like and Virginia tobacco-like, with sweet, rich, honey-like and cedarwood-like nuances.

The tobacco of the experimental cigarettes prior to smoking has a sweet, rich, honey-like, slightly fruity, hay tobacco-like, woody and cedarwood-like aroma nuances. The product of Example II produced according to the process of Example II enhances the tobacco-like taste and aroma of the blended cigarette imparting to it honey-like tobacco notes.

EXAMPLE VIII

Perfumed Liquid Detergent

Concentrated liquid detergents with floral and rose-oil like aromas are prepared containing 0.10%, 0.15% and 0.20% of 3-(methylthio)-1-(2,6,6-trimethyl-1,3-cyclohexadien-1-yl)-1-butanone prepared according to Example II. They are prepared by adding and homogeneously mixing the appropriate quantity of 3-(methylthio)-1-(2,6,6-trimethyl-1,3-cyclohexadien-1-yl)-1-butanone in the liquid detergents. The detergents all possess a floral, and rose-oil like fragrance, the intensity increasing with greater concentrations of 3-(methylthio)-1-(2,6,6-trimethyl-1,3-cyclohexadien-1-yl)-1-butanone.

EXAMPLE IX

Preparation of a Cologne and Handkerchief Perfume 3-(Methylthio)-1-(2,6,6-trimethyl-1,3-cyclohexadien-1-yl)-1-butanone prepared according to the process of Example II is incorporated in a cologne at a concentration of 2.5% in 85% aqueous ethanol; and into a handkerchief perfume at a concentration of 20% (in 95% aqueous ethanol). A distinct and definite floral and rose-oil like aroma is imparted to the cologne and to the handkerchief perfume.

EXAMPLE X

Preparation of a Cologne and Handkerchief Perfume

The composition of Example VI is incorporated in a cologne at a concentration of 2.5% in 85% aqueous ethanol; and into a handkerchief perfume at a concentration of 20% (in 95% aqueous ethanol). The use of the 2,2,6-trimethyl-1-[3-methylthio) butyryl]-1,3-cyclohexadiene in the composition of Example VI affords a distinct and definite strong floral, rose oil-like aroma to the handkerchief perfume and to the cologne.

EXAMPLE XI

Preparation of Soap Composition

One hundred grams of soap chips are mixed with one gram of 3-(methylthio)-1-(2,6,6-trimethyl-1,3-cyclohexadien-1-yl)-1-butanone produced according to the process of Example II until a substantially homogeneous composition is obtained. The perfumed soap composition manifests an excellent floral and rose oil-like aroma.

EXAMPLE XII

Preparation of a Detergent Composition

A total of 100 g of a detergent powder is mixed with 0.15 g of the 3-(methylthio)-1-(2,6,6-trimethyl-1,3-cyclohexadien-1-yl)-1-butanone of Example II until a substantially homogeneous composition is obtained. This composition has an excellent floral, rose oil-like aroma.

EXAMPLE XIII

A. Powder Flavor Composition

20 Grams of the flavor composition of Example IV containing 3-(methylthio)-1-(2,6,6,-trimethyl-1,3-cyclohexadien-yl)-1-butanone is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F., and a wheel speed of 50,000 r.p.m.

B. Sustained Release Flavor

The following mixture is prepared:

| Ingredient | Parts by Weight |
| --- | --- |
| Liquid Raspberry Flavor composition of Example IV containing 3-(methylthio)-1-(2,6,6-trimethyl-1,3-cyclohexadiene-1-yl)-1-butanone | 20 |
| Propylene glycol | 9 |
| Cab-OSil ® M-5 (Brand of Silica produced by the Cabot Corporation of 125 High Street, Boston, Mass. 02110; Physical Properties: Sulface Area: 200 m²/gm Nominal particle size: 0.012 microns Density: 2.3 lbs/cu.ft.) | 5.00 |

The Cab-O-Sil ® is dispersed in the liquid raspberry flavor composition of Example IV with vigorous stirring, thereby resulting in a viscous liquid. 71 Parts by weight of the powder flavor composition of Part A, supra, is then blended into the said viscous liquid, with stirring at 25° C. for a period of 30 minutes resulting in a dry, free flowing sustained release flavor powder.

EXAMPLE XIV

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example IV containing 3-(methylthio)-1-(2,6,6,-trimethyl-1,3-cyclohexadien-1-yl)-1-butanone is added to the solution which is then homogenized to form an emulsion having particle size typically in the range of 2-5 microns. This material is kept at 120° F. under which conditions the gelatin will not gel.

Coascervation is induced by adding, slowly and uniformly 40 parts by weight of a 20% aqueous solution of sodium sulphate. During coascervation, the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting gelled coascervate may be filtered and washed with water at temperatures below the melting point of gelatin, to remove the salt.

Hardening of the filtered cake, in this examle, is effected by washing with 200 parts by weight of 37% solution of formaldehyde in water. The cake is then washed to remove residual formaldehyde.

EXAMPLE XV

Chewing Gum

100 Parts by weight of chicle are mixed with 4 parts by weight of the flavor prepared in accordance with Example XIII. 300 parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE XVI

Chewing Gum

100 Parts by weight of chicle are mixed with 18 parts by weight of the flavor prepared in accordance with Example XIV. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant long lasting raspberry flavor.

EXAMPLE XVII

Toothpaste Formulation

The following separate groups of ingredients are prepared:

| Parts by Weight | Ingredient |
| --- | --- |
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Discalcium Phosphate (Dihydrate) |
| Group "C" | |
| 2.000 | Sodium N-Lauroyl Sarcosinate (foaming agent) |
| Group "D" | |
| 1.200 | Flavor Material of Example XIII |
| 100.00 (Total) | |

Procedure

1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant raspberry flavor, of constant strong intensity throughout said procedure (1-1.5 minutes).

EXAMPLE XVIII

Chewable Vitamin Tablets

The flavor material produced according to the process of Example XIV is added to a Chewable Vitamin Tablet Formulation at a rate of 10 gm/Kg which Chewable Vitamin Tablet Formulation is prepared as follows:

In a Hobart Mixer, the following materials are blended to homogeneity:

| | Gmns/1000 tablets |
| --- | --- |
| Vitamin C (ascorbic acid) as ascorbic acid-sodium ascorbate mixture 1:1 | 70.0 |
| Vitamin $B_1$ (thiamine mononitrate) as Rocoat ® thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example XIV | (as indicated above) |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong raspberry flavor for a period of 12 minutes.

EXAMPLE XIX

Chewing Tobacco

Onto 100 pounds of tobacco for chewing (85% Wisconsin leaf and 15% Pennsylvania leaf) the following casing is sprayed at a rate of 30%:

| Ingredients | Parts by Weight |
| --- | --- |
| Corn Syrup | 60 |
| Licorice | 10 |
| Glycerine | 20 |
| Fig Juice | 4.6 |
| Prune Juice | 5 |
| Flavor Material of Example XIII | 0.4 |

The resultant product is redried to a moisture content of 20%. On chewing, this tobacco has an excellent substantially consistent, long-lasting raspberry (20 minutes) nuance in conjunction with the main fruity tobacco note.

EXAMPLE XX

Tobacco Formulation

A tobacco mixture is produced by admixing the following ingredients:

| Ingredient | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
|---|---|
| Ethyl butyrateZ | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of 1-[3-(methylthio)butyryl]-2,6,6-trimethyl-cyclchexene produced according to the process of Example III. The control cigarettes not containing the 1-[3-(methylthio)-butyryl]-2,6,6-trimethyl-cyclohexene produced according to the process of Example III and the experimental cigarettes which contain the 1-[3-(methylthio)butyryl]-2,6,6-trimethyl-cyclohexene produced according to the process of Example III are evaluated by paired comparison and the results are as follows:

The experimental cigarettes prior to smoking are found to have a rich sweet flavor effect with lingering sweetness with fruity, blackcurrant-like, raspberry-like, dried fruit-like, and damascenone-like notes, and to have, on smoking, more tobacco-like, sweet-fruity and damascenone-like notes and to have more body than the control cigarettes.

The tobacco of the experimental cigarettes, prior to smoking, has sweet, floral, fruity, earthy and green notes. All cigarettes are evaluated for smoke flavor with a 20 mm cellulose acetate filter.

The 1-[3-(methylthio)butyryl]-2,6,6-trimethyl-cyclohexene produced according to the process of Example II enhances the sweet tobacco-like, fruity aromatic taste and aroma of the blended cigarette imparting to it.

BRIEF DESCRIPTION OF THE DRAWINGS

FIG. 5 is the infra-red spectrum for the compound synthetically produced according to Example II, and extracted from black tobacco leaf according to Example I, having the name 3-(methylthio)-1-(2,6,6-trimethyl-1,3-cyclohexadien-1-yl)-1-butanone.

FIG. 6 is the NMR spectrum for the compound synthetically produced according to Example III, and extracted from black tobacco leaf according to Example I, and named 1-[3-(methylthio)butyryl]-2,6,6-trimethyl-cyclohexene-1.

FIG. 7 is the infra-red spectrum for the compound synthetically prepared according to Example III, and extracted from black tobacco leaf according to Example I, having the name 1-[3-(methylthio)butyryl]-2,6,6-trimethyl-cyclohexene-1.

what is claimed is

Figure 1:
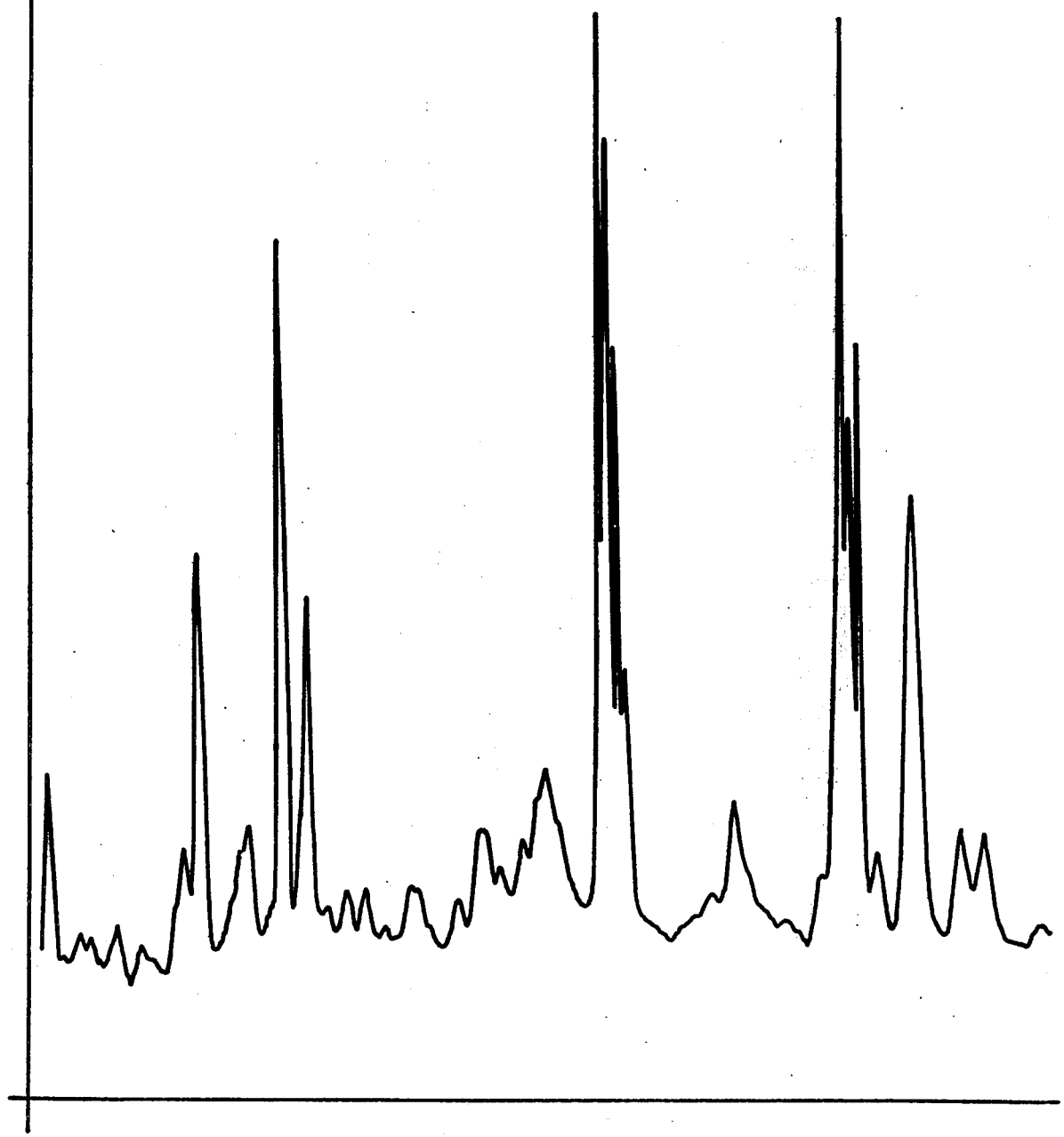
FIG. 1 is the GLC profile of that portion of extract of black tobacco leaf which includes the compounds of the present invention.
Figure 2:
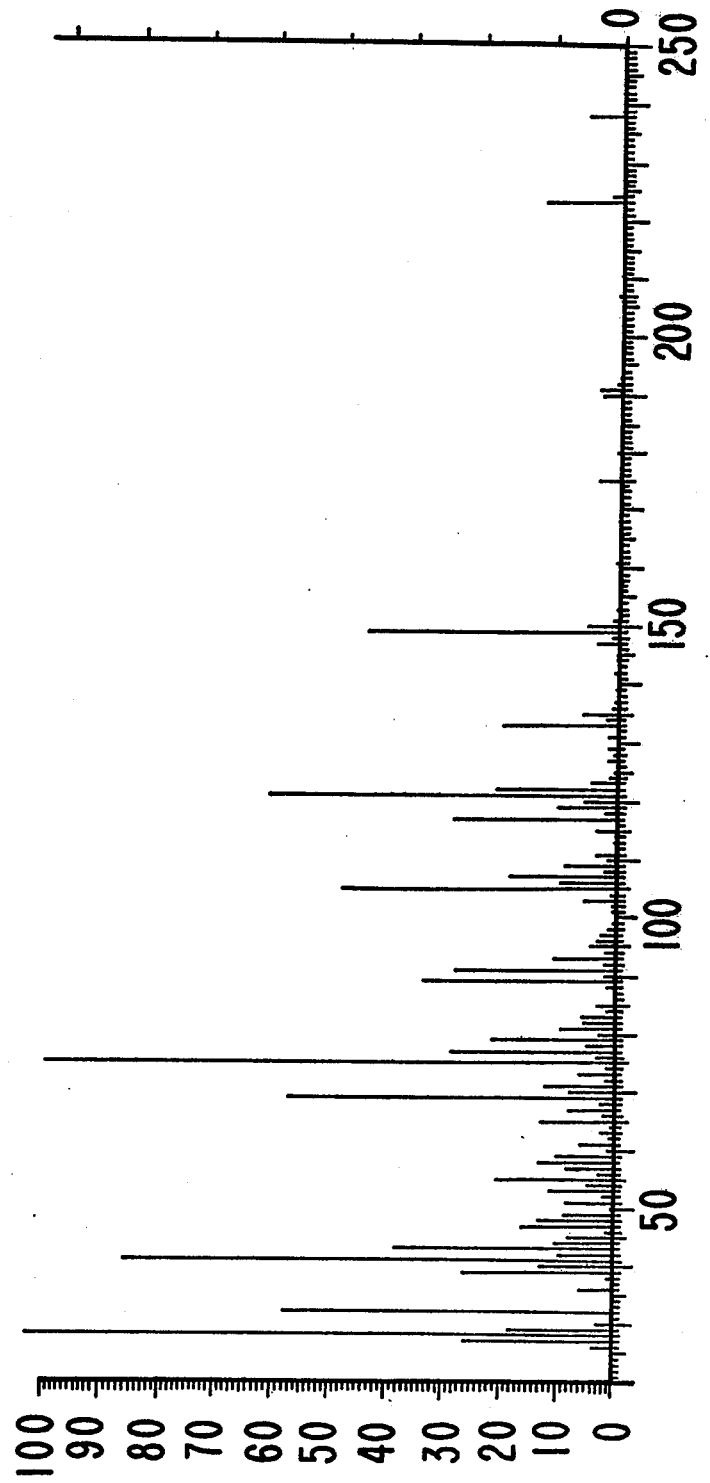
FIG. 2 is the mass spectral scan of peak A of the GLC profile of the extract of black tobacco leaf which consists of the compound 3-(methylthio)-1-(2,6,6-trimethyl-1,3-cyclohexadien-1-yl)-1-butanone
Figure 3:
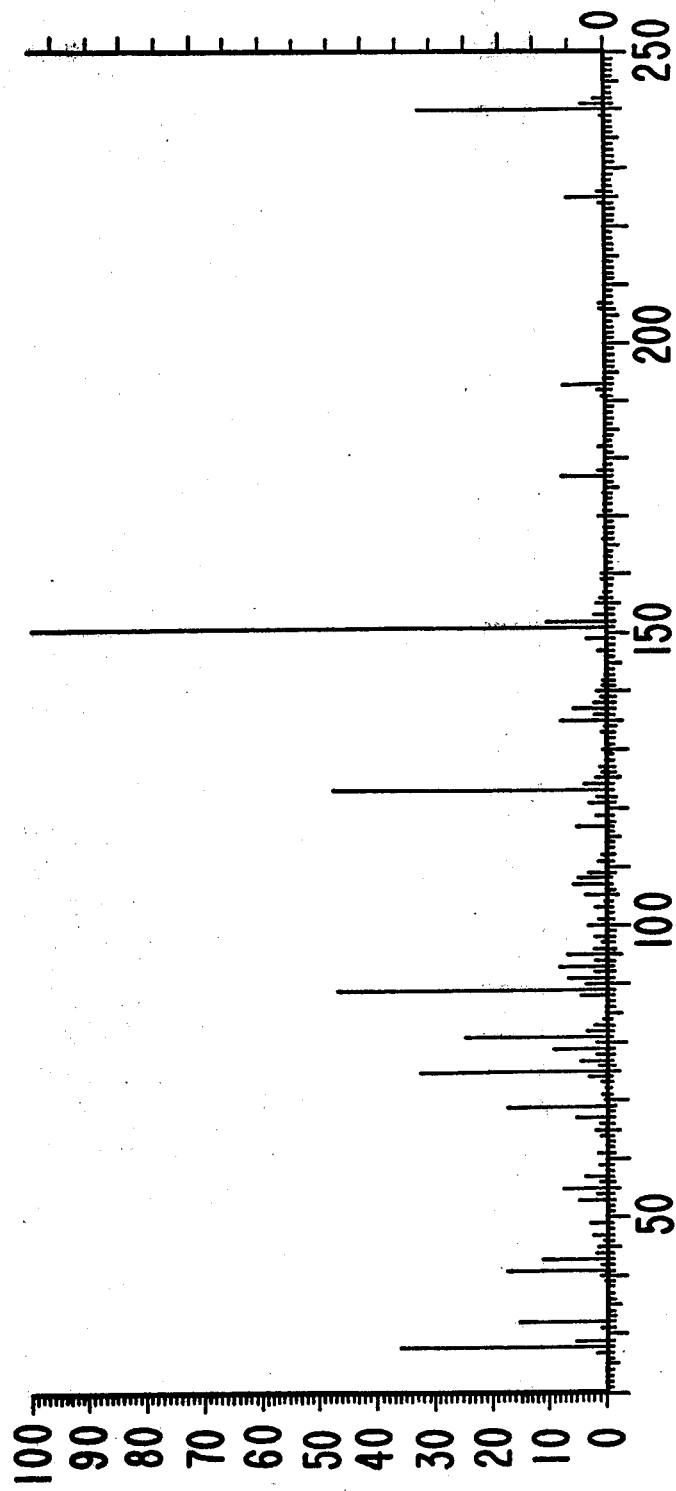
FIG. 3 is the mass spectral scan of peak B of the GLC profile of the extract of black tobacco leaf produced according to Example I which consists essentially of the compound 1-[3-(methylthio)-butyryl]-2,6,6-trimethyl-cyclohexene-1.
Figure 4:
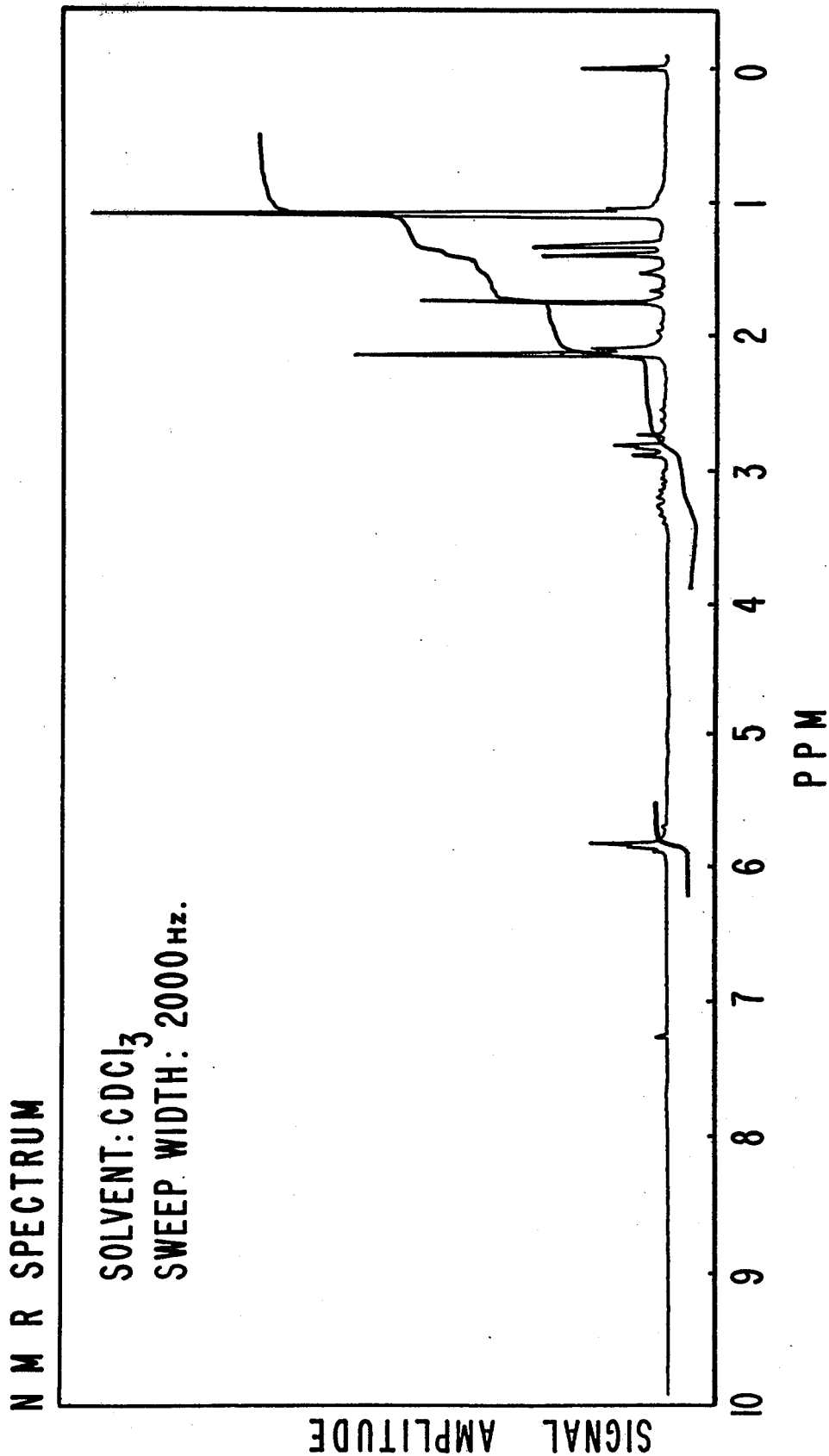
FIG. 4 is the NMR spectrum for the compound synthetically produced according to Example II and for the compound extracted from black tobacco leaf according to Example I, and named 3-(methylthio)-1-(2,6,6-trimethyl-1,3-cyclohexadien-1-yl)-1-butanone

1. A process for augmenting or enhancing the aroma of a perfume composition which comprises adding to said perfume composition a small but effective amount of a substantially pure, synthetically produced 1-(3-(methylthio)buryryl)-2,6,6-trimethyl-cyclohexene or the 1,3-cyclohexadiene analog defined by the structure:

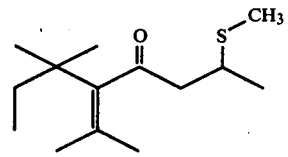

wherein the dashed line is a carbon-carbon single bond or a carbon-carbon double bond.

2. The process of claim 1 wherein in the analog the dashed line is a carbon-carbon double bond.

3. The process of claim 1 wherein in the analog the dashed line is a carbon-carbon single bond.

4. The fragrance modifying composition comprising a substantially pure, synthetically produced 1-(3-(methylthio)butyryl)-2,6,6-trimethyl-cyclohexene or the 1,3-cyclohexadiene analog defined by the structure:

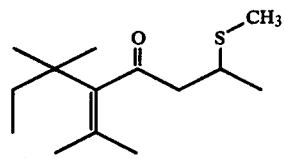

wherein the dashed line is a carbon-carbon single bond or a carbon-carbon double bond, and an auxiliary perfume ingredient compatible with said compound.

5. A perfume composition comprising a substantially pure, synthetically produced 1-(3-(methylthio)butyryl)-2,6,6-trimethyl-cyclohexene or the 1,3-cyclohexadiene analog defined by the structure:

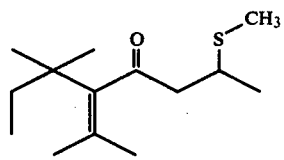

wherein the dashed line is a carbon-carbon single bond or a carbon-carbon double bond, and at least one adjuvant selected from the group consisting of natural perfume oils, synthetic perfume oils, nitriles, alcohols, aldehydes, other ketones, esters and lactones.

* * * * *

UNITED STATES PATENT OFFICE
CERTIFICATE OF CORRECTION

Patent No. 4,156,662  Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQUIN F. VINALS It is certified that error appears in the above-identified patent and that said Letters Patent are hereby corrected as shown below:

Title page, left-hand column, line 8:
"Louis S. Frederick" should read
---Frederick L. Schmitt---

Title page, right-hand column, line 4:  the structure:

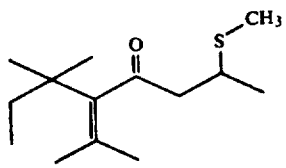

should be replaced with the structure:

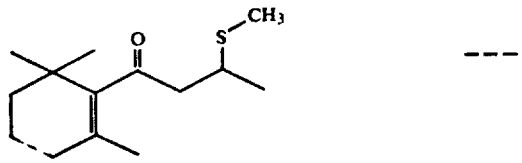

UNITED STATES PATENT OFFICE
CERTIFICATE OF CORRECTION

Patent No. 4,156,662  Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQUIN F. VINALS It is certified that error appears in the above-identified patent and that said Letters Patent are hereby corrected as shown below:

Title page, right-hand column, line 11: the structure:

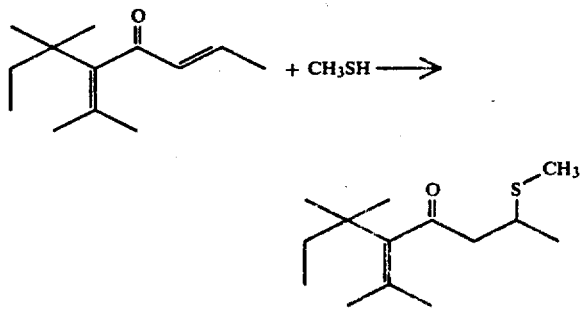

should be replaced with the structure:

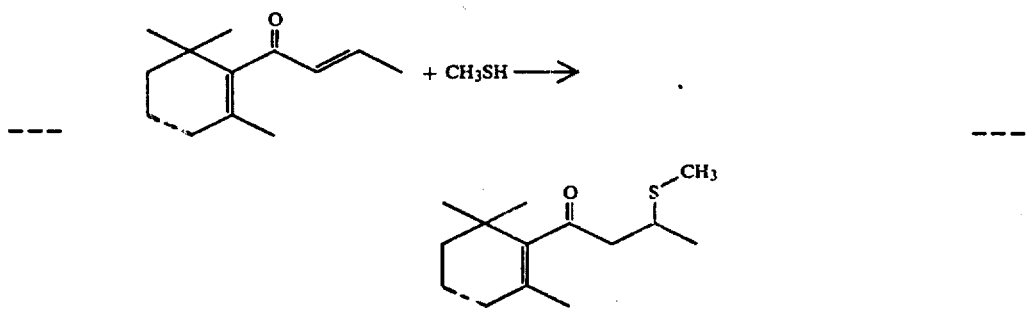

UNITED STATES PATENT OFFICE
CERTIFICATE OF CORRECTION

Patent No. 4,156,662  Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQUIN F. VINALS It is certified that error appears in the above-identified patent and that said Letters Patent are hereby corrected as shown below:

Column 1, line 20: the structure:

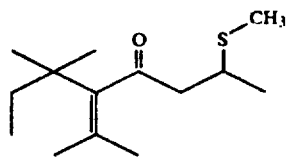

should be replaced with the structure:

--- 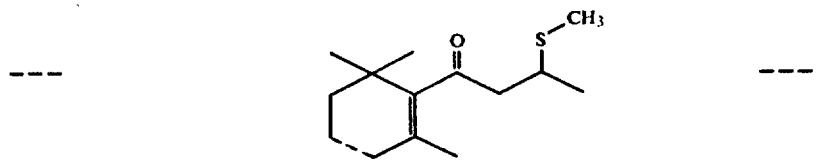 ---

UNITED STATES PATENT OFFICE
CERTIFICATE OF CORRECTION

Patent No. 4,156,662          Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQUIN F. VINALS It is certified that error appears in the above-identified patent and that said Letters Patent are hereby corrected as shown below:

Column 1, lines 30 to 35: the structure:

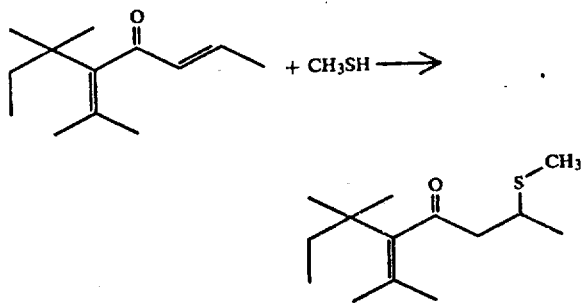

should be replaced with the structure:

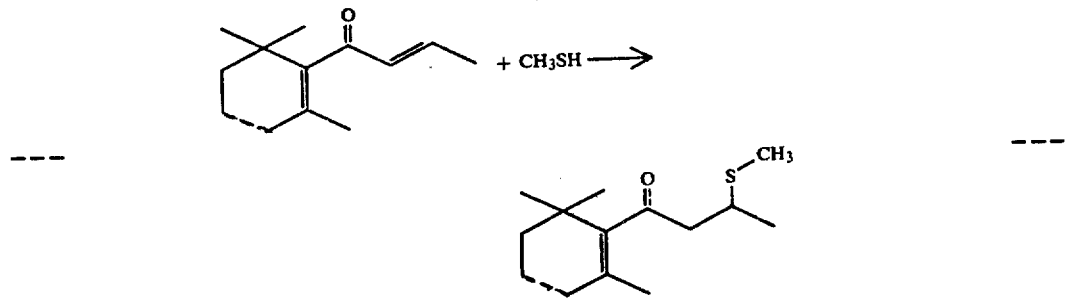

UNITED STATES PATENT OFFICE
CERTIFICATE OF CORRECTION

Patent No. 4,156,662    Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQUIN F. VINALS It is certified that error appears in the above-identified patent and that said Letters Patent are hereby corrected as shown below:

Column 3, line 20: the structure:

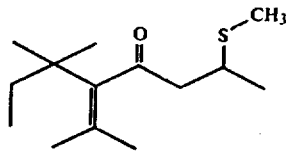

should be replaced with the structure:

--- 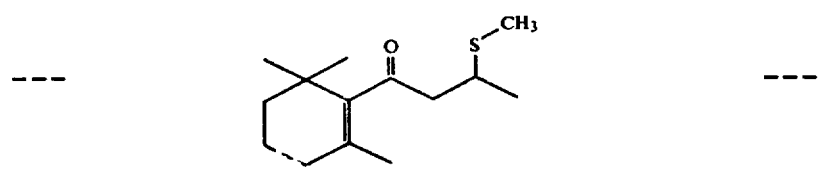 ---

Column 3, line 35: the structure:

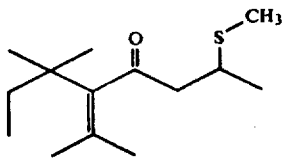

should be replaced with the structure:

--- 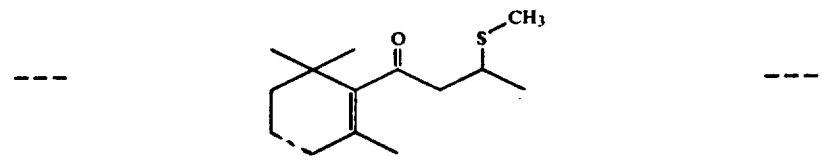 ---

UNITED STATES PATENT OFFICE
CERTIFICATE OF CORRECTION

Patent No. 4,156,662  Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQUIN F. VINALS It is certified that error appears in the above-identified patent and that said Letters Patent are hereby corrected as shown below:

Column 4, line 5:  the structure:

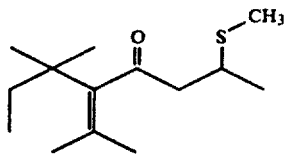

should be replaced with the structure:

--- 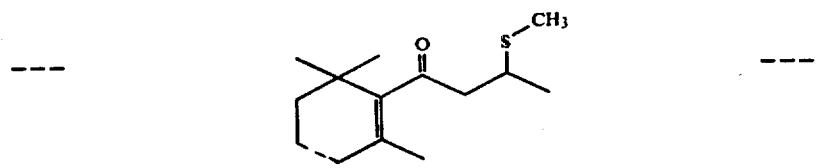 ---

UNITED STATES PATENT OFFICE
CERTIFICATE OF CORRECTION

Patent No. 4,156,662　　　　　Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQIN F. VINALS It is certified that error appears in the above-identified patent and that said Letters Patent are hereby corrected as shown below:

Column 4, lines 50 to 55: the structure:

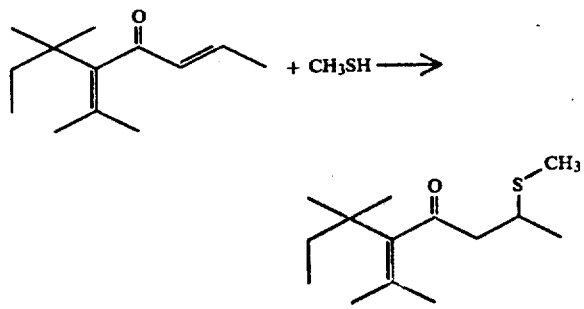

should be replaced with the structure:

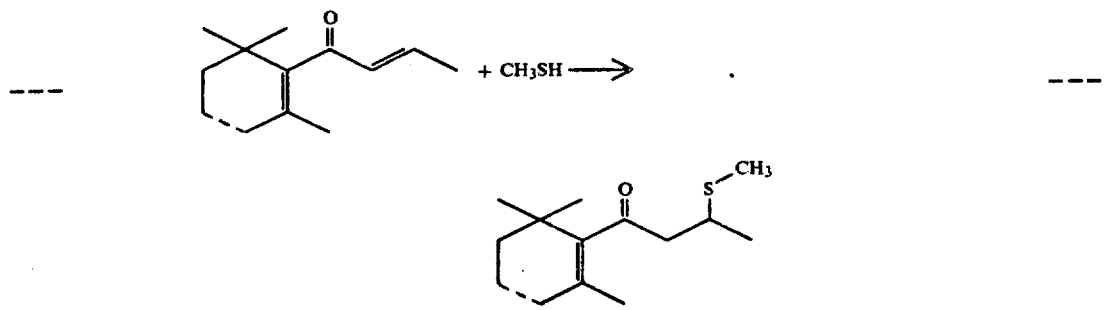

UNITED STATES PATENT OFFICE
CERTIFICATE OF CORRECTION

Patent No. 4,156,662                    Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQUIN F. VINALS It is certified that error appears in the above-identified patent and that said Letters Patent are hereby corrected as shown below:

Column 26, lines 25 to 30:  the structure:

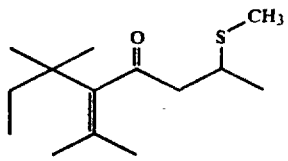

should be replaced with the structure:

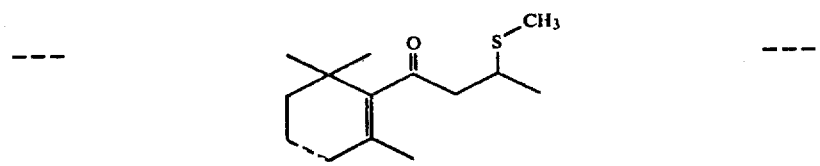

Column 26, line 45:  the structure:

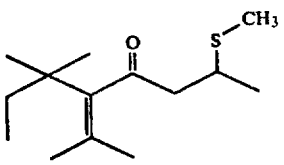

should be replaced with the structure:

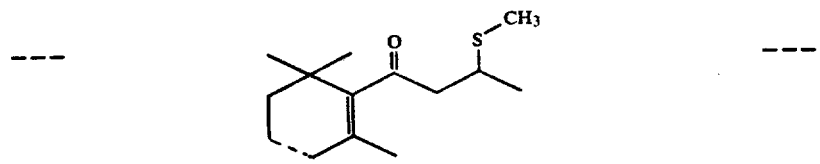

UNITED STATES PATENT OFFICE
CERTIFICATE OF CORRECTION

Patent No. 4,156,662        Dated May 29, 1979

Inventor(s) RICHARD A. WILSON, BRAJA D. MOOKHERJEE, ANNE S. HRUZA, MANFRED H. VOCK, FREDERICK L. SCHMITT, JOAQUIN F. VINALS It is certified that error appears in the above-identified patent and that said Letters Patent are hereby corrected as shown below:

Column 26, line 60: the structure:

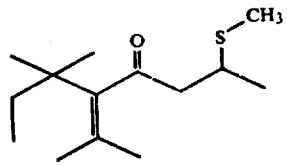

should be replaced with the structure:

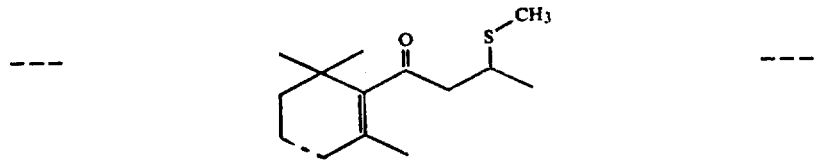

Signed and Sealed this

Twenty-third Day of October 1979

[SEAL]

Attest:

RUTH C. MASON
Attesting Officer

LUTRELLE F. PARKER
Acting Commissioner of Patents and Trademarks